(12) United States Patent
Sablón Carrazana et al.

(10) Patent No.: US 9,763,900 B2
(45) Date of Patent: Sep. 19, 2017

(54) CHEMICAL CHAPERONINS AS NOVEL MOLECULAR MODULATORS OF BETA PROTEIN AGGREGATION PRESENT IN CONFORMATIONAL DISEASES

(71) Applicant: Centro de Neurociencias de Cuba (NEURONIC), Havana (CU)

(72) Inventors: Marquiza Sablón Carrazana, Havana (CU); Chryslaine Rodriguez-Tanty, Havana (CU); Myriam Marlene Altamirano Bustamante, Distrito Federal (MX); Fernand Vedrenne Gutiérrez, Distrito Federal (MX); Suchitil Rivera Marrero, Havana (CU); Isaac Fernández Gómez, Estado de México (MX); Rosa María López Barroso, Havana (CU); Lina Andrea Rivillas Acevedo, Distrito Federal (MX); Reyna Lara Martinez, Estado de México (MX); Rafaela Perez Perera, Havana (CU); Alberto Bencomo Martínez, Artemisa (CU); María Guadalupe Domínguez Macouzet, Distrito Federal (MX); Luis Felipe Jiménez García, Distrito Federal (MX); Massiel Díaz Miranda, Havana (CU); Julio Morán Andrade, Distrito Federal (MX); Pedro Valdés Sosa, Havana (CU); Alejandro Perera Pintado, Havana (CU); Anaís Prats Capote, Havana (CU); Sergio Agustín Islas Andrade, Distrito Federal (MX)

(73) Assignee: CENTRO DE NEUROCIENCIAS DE CUBA, Havana (CU)

( * ) Notice: Subject to any disclaimer, the term of this patent is extended or adjusted under 35 U.S.C. 154(b) by 0 days.

(21) Appl. No.: 14/771,144

(22) PCT Filed: Dec. 30, 2013

(86) PCT No.: PCT/CU2013/000009
§ 371 (c)(1),
(2) Date: Dec. 9, 2015

(87) PCT Pub. No.: WO2014/131374
PCT Pub. Date: Sep. 4, 2014

(65) Prior Publication Data
US 2016/0106691 A1    Apr. 21, 2016

(30) Foreign Application Priority Data
Feb. 28, 2013  (CU) .................. 2013-0027

(51) Int. Cl.
*A61K 31/19*   (2006.01)
*A61K 31/167*  (2006.01)
(Continued)

(52) U.S. Cl.
CPC .......... *A61K 31/167* (2013.01); *A61K 31/197* (2013.01); *A61K 31/27* (2013.01)

(58) Field of Classification Search
USPC ....................................... 514/557
See application file for complete search history.

(56) References Cited

U.S. PATENT DOCUMENTS

| 7,799,782 B2 * | 9/2010 | Munson | C07D 231/56 |
| | | | 514/234.5 |
| 2012/0321560 A1 * | 12/2012 | Carrazana | C07C 43/225 |
| | | | 424/1.81 |

* cited by examiner

*Primary Examiner* — Rei-Tsang Shiao
(74) *Attorney, Agent, or Firm* — Lackenbach Siegel, LLP

(57) ABSTRACT

This invention relates to chemistry and biochemistry applied to the field of medicine and is referred to a new method of prevention and therapeutic treatment of conformational diseases (CD), in particular to amyloid origin diseases by administrating an effective amount of one or more compounds, salts, prodrugs or solvates, which are considered herein as chemical chaperonins, of Formula I,

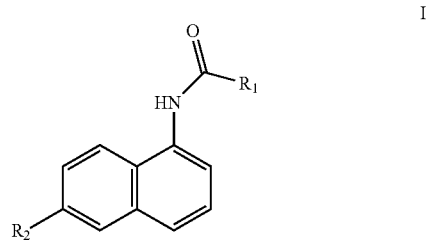

Where: $R_1$: -alkylenyl-C(O)NH-alkylenyl-$R_3$, -alkylenyl-C(O)O—$R_4$;
$R_3$: —COOH, —OH, —SH, —$NH_2$, —NH-alkyl-, —NH-dithiocarbamate-alkyl, —N-alkyl-dithiocarbamate alkaline earth metal salts.
$R_4$: succinimidyl group.
$R_2$: —H, -alkyl; wherein the term "alkyl" is characterized by a linear or branched aliphatic chain, hydrogen and saturated carbon atoms, comprising a methyl, ethyl, n-propyl, iso-propyl, n-butyl or iso-butyl groups. Wherein, the term "alkylenyl" refers to a divalent analog of a linear or branched alkyl group, preferably ethylenyl (—$CH_2CH_2$—) or butylenyl (—$CH_2CH_2CH_2CH_2$—) radicals. These compounds are neutral, lipophilic, and have low molecular weight. The present invention provides a novel method for CD prevention and therapeutic treatment, by inhibition, reduction and breakdown of prefibril, protofibril, amyloid fiber and plaque structures, all of them characterized by presenting cross-β-toxic structures (e.g. Alzheimer disease (AD), Parkinson's disease (PD), Diabetes Mellitus Type II (DM2), etc.), through the administration of the Formula I compounds,
(Continued)

which are considered herein as chemical chaperonins, in any acceptable pharmaceutical composition of one or more compounds or salts thereof, prodrug or solvate, that are capable of inhibiting, reducing, removing, etc., the formation of these structures which cause a protein misfolding, as well as to disaggregate fibers already formed.

7 Claims, 15 Drawing Sheets

(51) Int. Cl.
*A61K 31/197* (2006.01)
*A61K 31/27* (2006.01)

| Chemical Structure of chaperonins. | IUPAC Name Classification |
|---|---|
| | N-(2-aminoethyl)-N'-1-naphthylsuccinamide<br><br>A |
| | methyl (2-{[4-(1-naphthylamino)-4-oxobutanoyl]amino}ethyl)dithiocarbamate.<br><br>B |
| | (2R)-2-(6-methoxy-2-naphthyl)propanoic acid (Naproxen).<br><br>C |
| | N-[4-(1-naphthylamino)-4-oxobutanoyl]-b-alanine.<br><br>D |
| | 6-{[4-(1-naphthylamino)-4-oxobutanoyl]amino}hexanoic acid<br><br>E |
| | $N^3,N^{3'}$-ethane-1,2-diylbis($N^1$-1-naphthylsuccinamide).<br><br>F |
| | N-(4-aminobutyl)-N'-1-naphthylsuccinamide - ethane (1:1).<br><br>G |
| | (1E,6E)-1,8-bis(4-hydroxy-3-methoxyphenyl)octa-1,6-diene-3,5-dione - ethane (1:1). Curcumin |

Figure 1

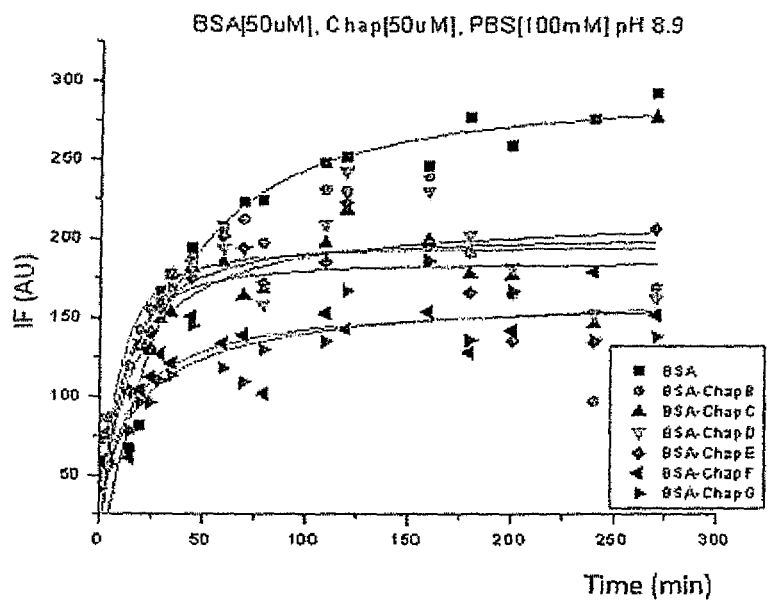
Part A
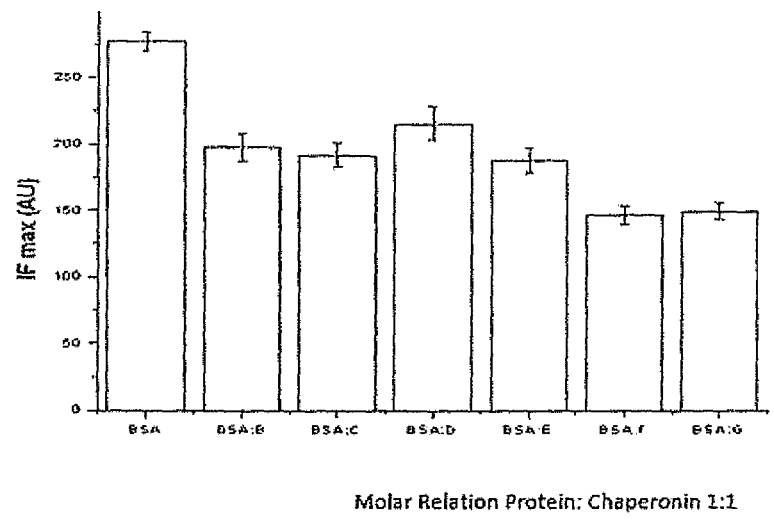
Part B
Figure 6

| inhibitors | % inhibition= a+b log [Chap] | | | IC50 (µM) |
|---|---|---|---|---|
| | a | b | $R^2$ | |
| ChapA | -7,89359 | 26,87674 | 0,98313 | 142,6 |
| ChapB | 0,10182 | 23,50494 | 0,93239 | 132,7 |
| ChapC | 23,42795 | 15,73676 | 0,9397 | 48,8 |
| ChapD | 1,70495 | 14,25195 | 0,79675 | 2447,2 |

Figure 8.

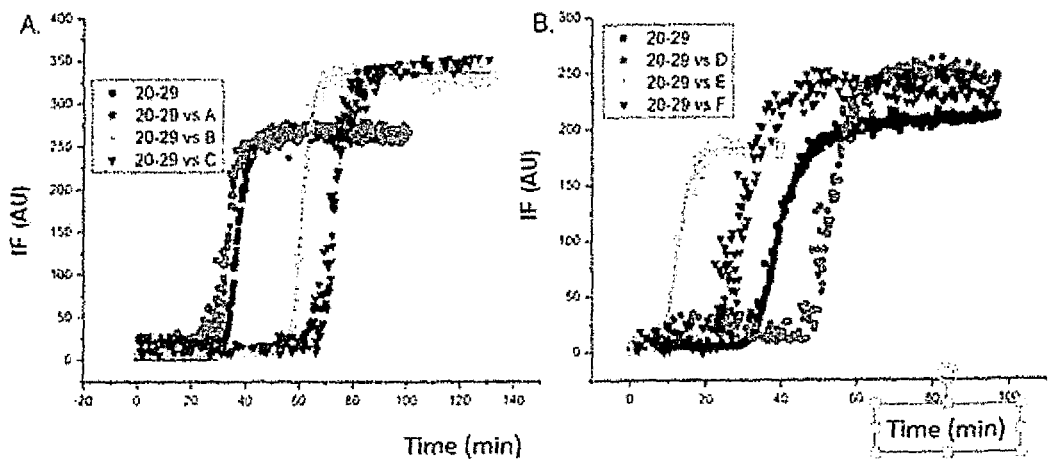
Part A
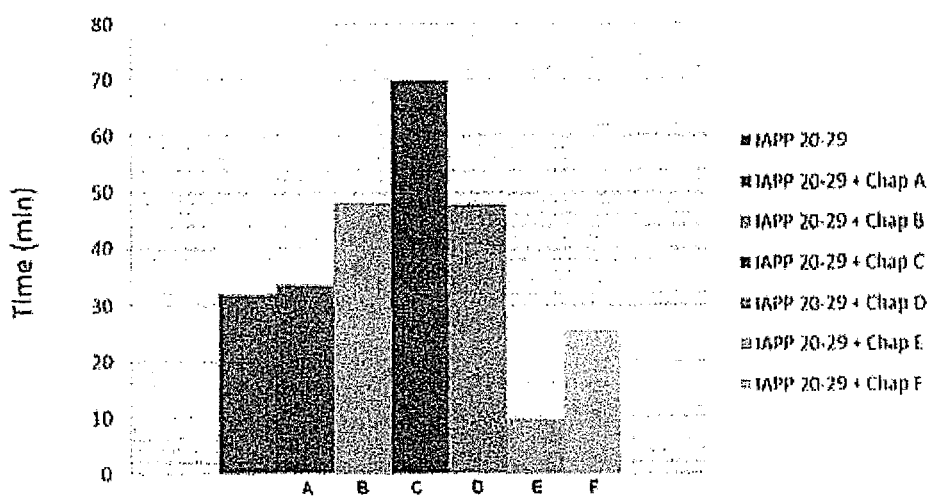
Part B
Figure 10

IAPP 20-29 50uM; ChapB 50, 100 y 500uM; PBS 100mM pH 7.4, NaCl 100M

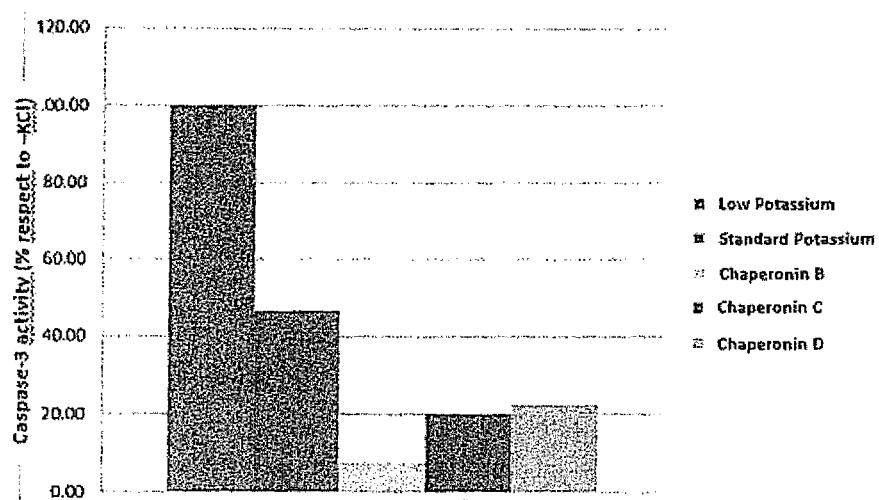
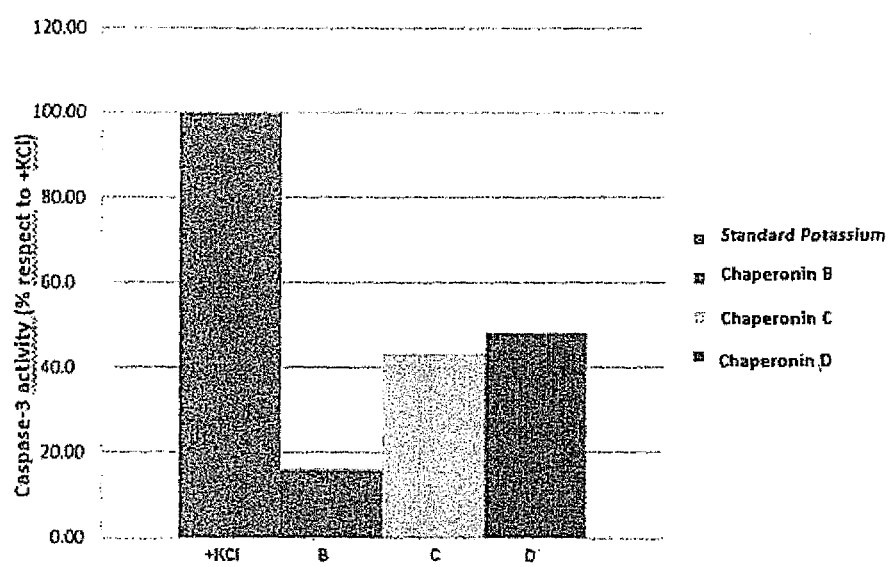
Figure 14.

CHEMICAL CHAPERONINS AS NOVEL MOLECULAR MODULATORS OF BETA PROTEIN AGGREGATION PRESENT IN CONFORMATIONAL DISEASES

This application claims priority to and is a U.S. 371 National Phase Patent Application of PCT Patent Application, Serial No. PCT/CU2013/000009, filed Dec. 12, 2013 which claims priority to Cuban application 2013-0027, filed Feb. 28, 2013 the contents of which are fully incorporated herein by reference thereto.

This invention relates to chemistry and biochemistry as applied to the field of medicine. It refers to a new method to inhibit, reduce or prevent the formation of cross-βtoxic structures: prefibrils, protofibrils, amyloid plaques and fibers present in Conformational Disease (CD) (Table 1), in particular, those having amyloid origin, by administering one or more compounds of Formula I, considered chemical chaperonins capable of inhibiting, reducing, disaggregate, refold and prevent the formation of the above mentioned structures between others.

The CD defined by Carrell et al. (Lancet 1997, 350, 134-138), bring together a number of different diseases that currently pose a challenge to medicine in terms of diagnosis, treatment and prevention. These diseases are characterized by an alteration in their structures, resulting in the onset of the formation of amyloid fibrils and its deposition in tissues. The expression of these diseases can be linked either to the toxic activity of the fibrillar intermediary, called oligomers, or loss of the biological function of the protein in its native state. Although there is no homology in the amino acid sequence of the various proteins involved in the CD, these diseases share, from the molecular point of view, the same pathophysiology, which involves a process of misfolding of the protein in question and its accumulation in the form of fibers.

At an early stage, these proteins may form oligomers and protofibrils, which give rise to the fibers that, depending on the affected organ and cytotoxicity of each of these structures; it promotes the delayed or episodic onset of these diseases (Carrell, R W. and Lomas, D A Lancet, 1997, 350, 134-138). There have been reported more than 15 proteins that can form these amyloid fibrils clearly associated with various pathological conditions. A non-exhaustive list of various CD together with its target protein is presented in Table 1.

TABLE 1

Some proteins associated with conformational diseases. (Chiti,F. and Dobson, C M Annu Rev Biochem 2006, 75, 333-66; Surguchev, A and Surguchov, A. Brain Res Bull 2010, 81: 12-24; Gaestel, M., Molecular Chaperones in Health and Disease, HEP, 2006,172: 1-42, Springer-Verlag Berlin Heidelberg).

| Protein | Disease |
|---|---|
| ABri | British family Dementia |
| ADan | family Danish Dementia |
| Amylin | Diabetes Mellitus Type 2 |
| Primary systemic amyloidosis | immunoglobulin light chains |
| Antithrombin | thromboembolic disease |
| Apolipoprotein A1 | familial polyneuropathy amyloid |
| Apolipoprotein AII | amyloidosis ApoAII |
| Apolipoprotein AIV | Amyloidosis apoAIV |
| Ataxin | spinocerebellar ataxia |
| Ataxinpoly -glutamine | spinocerebellar ataxias |
| Calcitonin | medullary thyroid carcinoma |
| cystatin C | Hereditary cerebral angiopathy |
| Cytokeratin | macular amyloidosis |
| γ - Crystal | Cataracts |
| Atrial natriuretic factor | atrial amyloidosis |
| Phenylalanine hydroxylase | Phenylketonuria |
| Fibrillin | Marfan Syndrome |
| Fibrinogen | hereditary renal amyloidosis fibrinogenic Amyloidosis |
| Fragments of the serum A amyloid protein | amyloidosis AA Familial Mediterranean Fever |
| gelsolin | Finnish hereditary systemic amyloidosis |
| hemoglobin | Sickle cell |
| Poly -glutamine huntingtin | Huntington's Disease |
| C1 inhibitor | C1 inhibitor for Angioedema deficiency |
| Lactoferrin | Corneal amyloidosis Lactoferrin |
| Lysozyme | visceral familial amyloidosis |
| Mutant lysozyme | amyloidosis Lysozyme |
| Mutant β -amyloid peptide | hereditary cerebral hemorrhage with amyloidosis |
| p53 | Cancer |
| β -amyloid peptide | Alzheimer Inclusion body myositis glaucoma |
| Prolactin | Prolactinoma Pituitary Amyloidosis APro |
| Glial fibrillary acidic protein | Alexander Syndrome |
| Protein C of pulmonary surfactant | Pulmonary alveolar proteinosis |
| Prion protein | Spongiform encephalopathies |
| keratins | Cutaneous lichen amyloidosis |
| Androgen receptor | Spinal and bulbar muscular atrophy |
| rhodopsin | Retinitis pigmentosa |
| Superoxide dismutase 1 | amyotrophic lateral sclerosis |
| Tau | frontotemporal dementia with parkinsonism |
| transthyretin | Senile systemic amyloidosis Familial amyloid polyneuropathy |
| α -1 antitrypsin | emphysema |
| α - synuclein | Parkinson Dementia with Lewy bodies |
| β2 - microglobulin | amyloidosis associated with hemodialysis |
| γ -crystalline | Cataracts |

It has been reported that oligomers are toxic at the cellular level, regardless of the amyloid protein from which they are formed. This demonstrates that the cytotoxic effect is a common molecular mechanism in all cases (Bucciantini M. et al in Nature 2002, 416: 507-511; Walsh D M and Selkoe D J in J Neurochem 2007, 101, 1172-1184; Yankner et al in Science 1990, 250, 279-282, Lorenzo et al. in Nature 1994, 368, 756-760, Pike et al. in Brain Res 1991, 563, 311-314, Lorenzo and Yankner in Proc. Natl. Acad. Sci 1994, 91, 12243-12247 and Schubert et al. in Proc. Natl. Acad. Sci USA 1995, 92, 1989-1993).

The predominant structure of amiloidogenic proteins is the cross-β sheet. This structure is stable in protein oligomerization and aggregation, which explains the entrenchment and deposit amyloid aggregates in various organs, causing tissue damage and organ dysfunction (B A Yanker et al Science 1990, 250, 279-282, Lorenzo and A. al in Nature 1994, 368, 756-760; O'Brien T D et al in Am J Pathol 1995, 147, 609-616, Ch J. Pike et al in Brain Res 1991, 563, 311-314; Lorenzo and Yanker B A A., in Proc Natl Acad Sci 1994, 91, 12243-12247; Schubert, D. et al in Proc Natl Acad Sci USA 1995, 92, 1989-1993).

The cross-βsheet formation is caused by multiple pathophysiological conditions that activate the production of these structures. These factors include altering the physicochemical properties of the protein caused by the temperature, ionic strength and pH changes. It can also be induced by proteolysis, phosphorylation and glycosylation. (Chaudhuri, T K and P. Subhandar, P. in FEBS Journal, 2006, 273, 1331-1349; Gaggelli E. et al in Chem Rev. 2006, 106: 1995-2044.)

Usually, in biological systems operating within normal parameters, the formation of protein aggregates is not observed because; in vivo the cell has different mechanisms to inhibit its formation, which is part of molecular machinery that is responsible for the degradation of proteins and protein complexes with misfolding. This machinery consists of the microtubular transport system, chaperones, chaperonins, the ubiquitin-proteasome system and autophagic vesicles. Understanding the nature of these protective processes together with the factors that inhibit and/or inactivate cellular regulatory machinery is crucial to develop strategies for CD prevention and treatment. (ZerovniK, E., in Current Alzheimer Research, 2010, 7, 74-83; Cohen, F. and Kelly, in J. Nature 2003, 426, 905-909)

Numerous studies show evidence of the interrelationship between these CD and especially between DM2 and AD (Nicolis, M R, in Curr Alzheimer Res 2004, 1 (1), 47-54, Squealed, J J et al in Clin. Med. (Barc.) 2008, 130 (12), 466-470, Nishimura, R. et al in Am J Kidney Dis 2003, 42 (1), 117-124; Pambianco, G. et al in Diabetes 2006. 55 (5), 1463-1469). DM2 is a metabolic disorder characterized by the progressive death of pancreatic β cells, the deposition of amylin cytotoxic amyloid fibers in target tissue and insulin resistance. Amylin, also known as IAPP, is a peptide of 37 amino acids secreted with insulin. Meanwhile, AD is characterized by the presence of amyloid plaques and neurofibrillary lattices in the brain. These neuropathological deposits are involved in the process leading to the progressive degeneration and neuronal death. (Zhao W Q and Townsend, M., in Biochimica et Biophysica Acta 2009, 1792, 482-496; Profenno, L. et al in Biol Psychiatry 2010, 67, 505-512). Senile plaques are found in the extracellular space of neurons and are mainly formed by deposits of β-amyloid peptides (βA) between 39 and 42 amino acids. (Gong et al in Proc. Natl. Acad. Sci USA 2003, 10 (18), 10417-22).

These amyloid structures have been therapeutic targets for the discovery of new treatments. Currently, investigations are directed to the search of pharmaceuticals capable of inhibiting, reducing or preventing the formation thereof. (Frisardi, V. et al in Ageing Research Reviews 2010, 9 (4), 399-417).

In the above-mentioned agents for controlling the CD are chaperones, which functions are to bind to nascent polypeptide chains to achieve the transient delay in its folding until synthesis is complete. (Benjamin I and Mc Millan D R in Circ Res 1998, 83: 117-32)

There are studies reporting the modulating or inhibitory action of these chaperones in the formation of structures with misfolding. These molecules can be classified into molecular, chemical and pharmacological. Mogk, A. et al. (EMBO J. 1999, 18, 6934-6949), Seong, I. S. et al. (FEBS Lett. 2000, 477, 224-229) and R. Zahn et al. (J. Mol Biol 1996, 261, 43-61) have evaluated in vitro various molecular chaperones (E. coli: IbpB, DnaK, DnaJ, GroEL, HtpG and SecB and A proteases as DegP, HsIU and Ion) and have proven that they prevent the aggregation and facilitate the fibril structure solubilization. In other studies carried out, (Schirmer E C et at in Trends Biochem Sci 1996, 21, 289-296. Sánchez, Y. et al in J. Bacteriol, 1993, 175, 6484-6491) there is evidence that Hsp40 chaperones, Hsp70, Hsp 100 and Hsp104 are involved in concert and they can be crucial in the disease progression by prion, so it has been postulated that even Hsp 104 could be a therapeutic candidate. However, no conclusive studies have been reported and are limited to in vitro and in vivo trials at the cellular level and in experimental animals without clarifying the risk/benefit ratio.

Moreover, it can be inhibited and correct the misfolding of mutated proteins through the use of other known chemical and pharmacological chaperones (Chaudhuri, T. Paul, S. in FEBS Journal 2006, 273, 1331-1349, and J P Morello al. in Trends Pharmacol Sci 2000, 21, 466-469). These molecules also called chaperonins, with low molecular weight, can stabilize the conformation of the proteins against thermal stress, inhibit the formation of misfolded structures and subsequently inhibit the formation of amyloid fibers. (H. Yoshida, et al. in Neurobiol. Dis. 2002, 10, 88-99). It has been shown that they can reverse the intracellular retention of different misfolded protein, as in the case of the transmembrane conductance regulator in cystic fibrosis, (Sato S. et al in J Bid Chem 1996, 271, 635-63, Tamarappoo B K and Verkman A S in J Clin Invest 1999, 101, 2257-2267), in the α-antitrypsin (Burrows J A J et al. in Proc Natl Acad Sci USA, 2000, 97, 1796-1801), in the aquaporin-2 (BK and Verkman A S Tamarappoo in J. Clin. Invest. 1999, 101, 2257-2267), in the receptor vasopressin V2 (Galkin Vekilov O. and PG in J. Mol. Biol 2004, 336, 43-59), in the galactosidase A (J P Chapple et al. in Trends Mol Med 2001, 7, 414-421), in the p-53 and the P-glycoprotein (Loo T W and Clarke D M in Chem 1997, 272, 709-712). Glycerol is an example of chemical chaperone, which has shown to increase the stability of a protein by decreasing the contact surface area thereof with the solvent (H. Yoshida et al. in Neurobiol. Dis. 2002, 10, 88-99; Reibekas A A and Massey V. in J Biol Chem 1997, 272, 22248-22252). There are other examples such as: dimethyl sulfoxide (DMSO), various quinacrines, N-octyl-h-valienamine (NOV), N-alkylated deoxynorjirimicine, 4-phenylbutyric acid, anthracyclines, porphyrins and azo compounds, and others. (H. Lin et at in Biochim Biophys Acta Mol Basis Dis 2004: 1-10; Sawkar A R et al. in Proc Natl Acad Sci USA 2002, 99, 15428-15433; J. A. J. Burrows et al. in Proc Natl Acad Sci USA 2000, 97, 1796-1801, Korth C., et al. in Proc Natl Acad Sci USA 2001, 98, 9836-9841, May in B C et al. in Proc. Natl Acad Sci USA 2003, 100, 3416-3421). Among the pharmacological chaperones are SR121463A, VPA985, 1-deoxygalactonojirimycin, CP31398, CP257042, capsaicin, cyclosporine, vinblastine and verapamil. (J P Morello et al. in Trends Pharmacol Sci 2000, 21, 466-469).

Most of these compounds have not been evaluated in humans as inhibitors of β-folding. Only quinacrine has been clinically approved and clinical trials have been conducted to evaluate the efficacy of this molecule in patients with Creutzfeldt-Jacob disease (Vogtherr M. et al in J. Med Chem 2003, 46, 3563-3564).

In the case of AD it has not been described an effective therapy based on the usage of chaperones, up to now.

The inhibition of Aβ fibrils formation is a reasonable therapeutic strategy. (Findies M A in Curr. Top Med Chem 2002, 2, 417-423. Yang D S et al. in Amyloid 2001, 8, 10-19) Thus, it is described in the literature, the in vitro evaluation of mimetic peptides, based on the LVFFA amino acid sequence from Aβ, modified in N- and C-terminal amino acids and their conversion into dextrorotatory and other retro-mimetic peptides, but its pharmacological application is still far from reality. (Chaudhuri, T. Paul, S. in FEBS Journal 2006, 273, 1331-1349, McFadden, F. in CA 2_A1 240.05; Fezoui, Y. and Jara-Soto, C. in U.S. 2007/0155955 A1).

There are also numerous patents related to the use of non-peptidic compounds, which use has been described as an inhibitor or destabilizing of amyloid fibers, however so far, they have not been totally effective against the therapeutic target.

Thus, Szarek et al patent (U.S. Pat. No. 5,869,469) claimed a method for modulating Aβ deposits in humans, with the administration of a compound or its pharmacologically acceptable salt, which contains a phosphonate group and a carboxylate. No experimental results that support the proposed are exposed.

Cooper, G. et al. in WO 03/063880 provides a method to block the toxicity of amyloid proteins in cells with the use of one or more polycyclic compounds. Among them, preferably the polyacenes, substituted or not, containing three or four rings. In particular, this invention describes the disruption methods for amylin transition (IAPP) from its soluble native structure to the oligomeric and/or insoluble fibrillar states, as well as the inhibition of the pre- or protofibrils amyloid aggregates and fibers. These compounds also decrease the production of the amyloid protein in a way that can be used in the prevention and treatment of pancreatic amyloidosis. In particular, a method for treating DM2 is described. Among the compounds used are quinacrine, chlorpromazine and tetracycline. Also, like other tetracycline related compounds, acridine, phenothiazines, anthracyclines, quinacrinas, chlorpromazine and Congo Red (CR).

On the other hand, K. Watanabe et al in U.S. Pat. No. 8,106,045 82, suggest that polycyclic compounds type 2-morpholino-4-pyrimidone and its derivatives may be effective in the prevention and treatment of AD caused by the tau protein over activity, claiming the action of these compounds against amyloid structures present in other neurodegenerative diseases, DM2 and certain neoplasias.

The use of aromatic polyhydroxylated derivatives for treating amyloidosis in AD and in diseases characterized by the presence of the α-synuclein protein fibrils in PD and in Lewy bodies, has been claimed in U.S. 2001 Patent/ 004703A21, by G. Castillo and collaborators. Likewise, the treatment of other amiloidogenic diseases, based on a method that may be effective to reduce, eliminate or prevent the formation of fibrillar deposits in brains of patients, is claimed. Among the tested compounds are: myricetin, exifone, pyrogallol, tannic acid, pyrocatechol, quercetin, ellagic acid, 1,2,4-benzenetriol, 5-hydroxydopamine trihydrate gallamida, gallic acid, ethyl gallate, quinic acid, and others.

Bode V. and Kurt L. (U.S. Pat. No. 5,637,571) announce the use of cetals of podophyllotoxin D-glucopyranoside and 4'-dimethylpodofilotoxin D-glucopyranoside, lignan derivatives, in the preparation of pharmaceutical compositions for the treatment or prophylaxis of amiloidogenics diseases, including AD. In 2007, it was published a patent (U.S. 2007/0015737 A1) by Clark A. et al. which claims the use of a wide range of organic compounds that possess an alkyl chain, comprising at most, two carbon atoms tri-substituted, with multiple variants. The substituent may be a single element (e.g., H, O, N), functional groups (e.g. esters), anionic groups or heterocycles of different complexity. Specifically, they reported as therapeutic compounds the 3-(3-hydroxy-1-propyl)amine-1-propanesulfonic acid, DL-2-amino-5-fosforovaleric acid, 4-phenyl-1-(3'-sulfopropyl-1, 2,3,6-tetrahydropyridine, cyclohexylsulfamic acid, phospho-L-serine, hexafluoroglutaric acid, 8-methoxyquinoline 5-sulfonic acid, 3-amino-2-hydroxy-1-propane sulfonic acid, 3-dimethylamino-1-propane sulfonic acid and its esters, acids or pharmaceutically acceptable salts. These compounds according to the authors can be used to inhibit, reduce or disrupt amyloid deposits in vivo. Thus, this invention provides a method and the pharmacology composition for treating amyloidosis.

Other types of molecules which bind specifically to insoluble amyloid protein deposits are the estirilbenzenes derivatives (Zhuang et al. in J Med Chem 2001, 44, 12, 1905-14) and pyridine (Kung et al in Mol Imaging Bid, 2003; 5, 6, 418-26). Also, stilbene derivatives showed by Kung et al. in WO 03018070 and WO 2006066104 have been effective as inhibitors of amyloid aggregation.

As a result of epidemiological studies, it is known that the use of non-steroidal anti-inflammatory drugs (NSAIDs) delays the onset of AD. (JCS Breitner et al in Neurobiol Aging 1995, 16, 523-530, Stewart W F et al in Neurology 1997; 48, 626-632, G P Lim et al in J. Neurosc 2001, 20, 15, 5709-5714; Rogers J. et al in Neurology 1993, 43: 1609-1611; Agdeppa E D et al in Neurosciences, 2003, 117, 723-730) All these drugs contain aromatic rings in their general structure. Various investigations aimed at finding molecules that can be used in diagnosis or treatment of AD are based on these chemical structures.

Some of these molecules have been labeled with $^{18}$F for the amyloid plaques detection by visualization techniques with encouraging results. (Shoghi-Jadid K et al in J. Am Geriatr Psychiatry 2002. 10, 24-35, Braskie M N et al in Neurobiol Aging 2010; 31, 10, 1669-1678; Barrio J R et al. in J. Nutr Health Aging 2008, 12, 1, 615-655 Henriksen G et al in Eur J Nucl Med. Mol imaging 2008, 35 (Suppl 1), 575-581).

In U.S. Pat. No. 5,276,059, entitled "Inhibition of diseases associated with the amyloid fibrils formation" proposes that the use of CR, a derivative thereof or a pharmaceutically acceptable salt thereof, may be employed for the treatment of diseases originated from the amiloidogenics fibers formation. This invention reports that the claimed compounds are capable of interfering with the amilodogenesis process or with the instability of the formed protein structure, preferably those involved in the tissues of the nervous system and in the pancreas in the case of DM2. During the 90s, last century, there were described results in which the in vitro inhibitory action of the CR against the Aβ deposits were corroborated (Burgevin et al in Neuro Report, 1994 5, 2429. Lorenzo and Yanker in Proc Natl Acad, Sci 1994, 91, 12243; Pollack at al in Neuroscience Letters, 1995 184, 113. Pollack et al, in Neuroscience Letters, 1995 197, 211). However, if this compound, its salts or its derivatives were going to be used in the treatment in vivo of any disease of the central nervous system, it would have to take into account that only 0.03% of CR is able to cross the blood brain barrier (BBB). (Tubis et al. in J. Amer. Pharm. Assn. 1960, 49, 422) It is also known that certain azo dyes may be carcinogenic (Morgan et al. in Environmental Health Perspectives 1994, 102 (Suppl.), 2, 63), so the therapeutic use of these compounds must be supported by larger studies.

Klunk W. et al describe in their patent (U.S. Pat. No. 6,133,259), the use of non-azo derivatives of Chrysamine G in pharmaceutical compositions, for the treatment and diagnosis of diseases caused by the onset of amiloidogenics fibers, such as AD, Down syndrome, DM2, Creutzfeld-Jacob, among others, The use of other aromatic compounds such as pamoic acid, derivatives and analogues are in Gallo et al patent. (WO0200603), for the treatment of diseases characterized by amyloid aggregates deposition. In particular, the pamoic acid is a naphthoic acid derivative having in its structure two-naphthyl groups. Minetti et al. in WO 2007045593 describe other naphthyl derivatives thet also inhibit amyloid aggregation and according to its inventors, they cross the BBB. Also, Hays et al. (WO 9716194) describe some naphthyl-azo compounds that inhibit amyloid aggregation too and can be used in pharmaceutical compositions for treating pathologies arising from these structures. So far, it has not been developed an effective treatment to delay the onset and/or progression of CDs (amyloidogenic), including AD and DM2. The Food Drug Administration of the United States (FDA) has approved the use of donepezil, galantamine or rivastigmine; however, these drugs do not stop the progress or reverse the neurodegenerative process of AD and are only effective temporarily for a few months or few years.

INVENTION SUMMARY

The present invention provides a novel method for prevention and therapeutic treatment of CDs and in particular, those having amyloid origin; through inhibition, reduction, disaggregation of the prefibrills, protofibrils, fibers and plaques structures, all characterized by the presence of cross-βtoxic structures, as mentioned in Table 1; among many others that may arise in the future by the compounds administration, considered herein as chemical chaperonins of Formula I. These compounds and their preparation methods are described in the Cuban Patent No. 2009-57, PCT-CU2010-000001, WO/2010/118706, EP 2436666 A20, and Patent Applications: Mexico No. 29/2011, Brazil 27/2011, USA 10/2012, Malaysia 12/2012, Japan 9/2012, Canada 7/2012, South Africa 18/12012, among others.

These compounds may be used in any acceptable pharmaceutical composition and administered by different ways, monotherapy or in combination with one or more compounds, salts, prodrugs or solvates which are capable of inhibiting, reducing, removing or disaggregation, among others, these structures obtained by misfolding protein. These compounds could also be administered to completely reverse the formation of such fibers.

As an extension of this invention, the treatment of diseases susceptible of benefiting from the biological activities exhibited by the compounds described herein, or a salt, derivative, prodrug or pharmaceutically acceptable solvate thereof, is included.

As used herein, the term "derivative" includes pharmaceutically acceptable compounds, i.e. Formula I derivatives compounds, that can be used in the obtainment of a drug, as well as unacceptable pharmaceutically derivatives, as these may be useful in the preparation of pharmaceutically acceptable derivatives.

The term "prodrug", as used herein, includes any compound derived from the Formula I compound for example esters, including carboxylic acid esters, amino acid esters, phosphate esters, sulphonate esters of metal salts, carbamates, amides; not limited to these examples, which is capable of providing, the Formula I compound directly or indirectly, when administered to an individual. Advantageously, this derivative is a compound that increases the bioavailability of Formula I compound when it is administered to an individual or that enhance the release of the Formula I compound in a biological compartment. The preparation of said prodrug may be performed by conventional methods known by experts in the field.

The invention compounds may be in crystalline form as free compounds or as solvates and it is intended that both forms will be within the scope of the present invention. In this regard, the term "solvate" as used herein, includes as pharmaceutically acceptable solvates, i.e., solvates of the compounds of Formula I which can be used in a drug manufacture, as pharmaceutically non-acceptable solvates, which may be useful in the preparation of pharmaceutically acceptable salts or solvates.

For its application in therapy, the Formula I compounds, their isomers, salts, prodrugs or solvates, will preferably be in an acceptable pharmaceutical form or substantially pure, i.e., having a pharmaceutically acceptable purity level, excluding normal pharmaceutical additives such as diluents and carriers, and also excluding toxic material at normal dosage levels. The purity levels for the active compound are preferably above 90%. In a preferred embodiment, they are above 95% of the Formula I compounds, or their salts, solvates or prodrugs.

The compounds of the invention, their pharmaceutically acceptable salts, prodrugs and/or solvates, and pharmaceutical compositions containing them, may be used together with other additional drugs to provide a combination therapy. This additional drugs can be part of the same pharmaceutical composition or, alternatively, can be provided as a separate composition for the administration, simultaneous or not, to the pharmaceutical composition comprising one or more Formula I compounds or a prodrug, solvate composition, derivative or a pharmaceutically acceptable salt thereof.

In the sense used in this description, the term "effective amount" refers to the amount of the agent or compound capable of developing specific therapeutic action by their pharmacological properties, calculated to produce the desired effect and in general it will be determined, among other causes, by the own characteristics of the compounds.

It should be considered the patient's clinical data such as age, patient condition, the severity of the disturbance or disorder, and the way and frequency of administration.

In the present invention, other objects, advantages and features will emerge from the descriptive and practice sections of this invention.

Definitions

Amiloidogenic protein. It refers to any polypeptide. Preferably, polypeptide that is unfolded or misfolded which requires to be retracted, alternatively it may be a folded polypeptide that is not maintained in its well-folded state or is forming protofibrils and amyloid fibers. Examples of polypeptides include those that are relevant in medicine and biotechnology as antibodies, insulin, amylin, amyloid β peptide, toxins, hormones, etc. (Table 1).

Folding Promotion: Refers to two situations. The first is the one in which the polypeptide to be replicated is in an unfolded or misfolding state or both. In this case, the correct refolding is promoted by the invention method. In the second situation, the misfolding peptide is already forming protofibrils and/or amyloid fibers and in this case, the method of invention serves to reduce and/or inhibit the formation of amyloid fibrils or protofibrils and to disaggregate and destroy the fibers already formed.

Chaperonin chemistry: Overall, is a chemical compound of low molecular weight, this though is not a constraint in its definition, which is involved in promoting protein folding in non-enzymatically way, and prevent abnormal conformations facilitating polypeptide structural alignment and correcting anomalies in process. It binds to the polypeptides that are unstable or in a non-native structural state, or a wrong secondary or tertiary structure. These chemical chaperonins include Formula I compounds.

Accumulation: In this case, storage of fibrillar peptides and/or their oligomeric precursors in the intra or extracellular space.

Aggregation: Relates to the polymerization of misfolded oligomers having the ability to form interactions between them.

Amyloidogenic: That has the property of forming fibers with cross-β structures.

Apoptosis: It is a cell death programmed process in which the cell is self-destructs in order to prevent the progression of damage, in both local and tissue levels.

Blood Brain Barrier (BBB): It is the separation between the circulatory system and the extracellular environment of the central nervous system. It consists of vascular cell walls formed by intimately united cells in the capillaries of the CNS.

Therapeutic targets: Organ, tissue, cell, receptor, gene, protein, or other, that are the therapeutic target or attack center for certain treatment.

Cytotoxic: Any compound that has the power to interfere with normal cellular processes, causing damage and sometimes cell death.

Azo compounds: Refers to compounds which contain an azo group (—N═N—) in their structure.

Conformation: Is the three-dimensional structure that adopts a chemical compound relative to the rotation that occurs through one or more single covalent bonds.

Functional Conformation: It refers to a protein structure, in which it can be performed all the functions for which it is designed.

Cell Control: Are the cellular mechanisms that are as function to keep its integrity and environment.

Derived: Substances chemically similar to a mother substance.

Naphthalene Derivatives: They are those chemical compounds that contain an aromatic bicyclic group equal to the naphthalene structure. This document relates to Formula I derivatives.

Conformational Diseases: Are the group of diseases which are based on pathophysiology fiber accumulation and toxic oligomers formation of a peptide or misfolding protein of cross-β conformation (Table 1).

Heat stress: It refers to the phenomenon in which cell damage occurs by exposure to temperatures above the optimum. During the thermal stress, enzymes and proteins are affected, generating cellular machinery damaged and in some cases cellular death.

Pharmaceutically acceptable: Regarding the salts that can be administered as therapeutic agents.

Glycosylation or glycosylation: Involves conjugation of amino groups, both terminal and laterals with molecules with mono, di and oligosaccharides.

Inhibition: Refers to a decrease in normal activity. In this case, refers to a decrease in the kinetics of peptides and proteins aggregation by the presence of a compound.

cross-β sheet. It is one of the secondary protein conformations in which several linear chains stabilize each other by cross interactions.

Modulation. It refers to the involvement of chaperonins in the misfolded peptides aggregation process. It can be positive or negative modulation.

Modulator. It refers to Formula I compounds that can inhibit, reduce, eliminate and disaggregate misfolding structures.

Monotherapy. It is the administration of a single substance to treat pathology.

Neurodegenerative. It is said that a neurodegenerative process occurs when bring about chronically the death or neuronal dysfunction.

Oligomer. They are high molecular weight soluble aggregates.

Amyloid Peptide. Relates to fibrous and insoluble aggregates which share several features, among which there is the high content of domains with cross-β sheet.

Senile plaques. These are amyloid proteins aggregates outside neurons.

Folding. It is the process by which a protein assumes its native conformation. Sometimes it is assisted by chaperonins.

Prefibrilar. Said of those aggregates and soluble oligomers that have not formed fibers.

Active Ingredient. It is a substance that has a biological effect in a pharmaceutical preparation.

Prodrug. Substances which can be converted to a drug in the human body with therapeutic activity.

Protofibrils. They are oligomer peptides, when interact with similar oligomers can give rise to fibers.

Administration. Ways in which a drug will enter the patient's body.

DISCLOSURE OF THE INVENTION

The following examples should not be construed in any way as limiting of the present invention. They illustrate the new prevention and therapeutic treatment method for CDs and particularly those having an amyloid origin (AD, DM2, EP, EH, ETT, among others), through inhibition, reduction, disaggregation of structures of prefibrills and protofibrils, amyloid plaques and fibers, with the use of Formula I compounds which are considered herein as chemical chaperonins.

DESCRIPTION OF THE FIGURES

FIG. 1: It shows the structures and the IUPAC name of the selected compounds, as non-limiting examples of the Formula I, which evaluations are exemplified, as well as the reference compounds used (naproxen and curcumin).

FIG. 6: It shows the kinetic of the BSA fibrils formation (50 μM) in the presence or not of chaperonins B, C, D, E, F and G, selected as non-limiting examples of Formula I (figure Part A) and the inhibitory effect (figure Part B) of the fibril formation by the action of these chaperonins at 50 µM, 75° C. in PBS (pH=8.9, 100 mM), measured by fluorescence spectroscopy with thioflavin-T (ThT 24 µM).

FIG. 8: It shows experimental $IC_{50}$ values for chaperonins A, B, C and D, determined from the inhibitory effect thereof on the BSA fibrillogenesis process (300 µM, molar ratio BSA:Chap 1:0, 1:0.01, 1:0.05, 1:0.5, 1:1, 1:2.5, 1:5) at 42° C. in glycine (pH=3, 50 mM, NaCl 100 mM) in the presence of ThT (24 µM).

FIG. 10: It shows the kinetics of fibril formation of the IAPP fragment 20-29 (100 µM) at 25° C. in PBS (pH 7.4, 100 mM, NaCl 100 mM) in the presence or absence of chaperonins A, B, C, D, E and F (100 µM), selected as Formula I non-limiting examples (figure Part A) and the inhibitory effect (Part B) of the fibril formation by the action of these chaperonins. Molar ratio IAPP:ThT, 50:1.

FIG. 14: Evaluation of the protective activity and/or reconditioned of the chaperonins B, C and D, as Formula I non-limiting examples, when administered to rat Cerebellar Granular (CGC) cell cultures, which at the same time, are subjected to a low potassium medium, −KCl. Part A of the figure presents the results with respect to the −KCl control (protective effect) and Part B presents the results regarding the control of standard potassium+KCl (reconditioned effect).

Example 1—Evaluation of the Modulator Character of Chaperonins in HSA Fiber Formation by Transmission Electron Microscopy (TEM)

The preparation of the samples was performed at a final concentration of 3.017 mM of HSA in Tris buffer (pH=7.4, 20 mM) in the presence or not of the chaperonin A (3.017 mM and 9.051 mM). Incubated at 65° C. for 72 hours. Aliquots were taken every 2 h for TEM study.

HSA solution (5 ul) is placed in 300 mesh copper grids formvar covered for 3 minutes. The excess solution is removed with a micropipette. Subsequently uranyl (5 uL, 2%) is added previously centrifuged at 12,000 rpm for 10 minutes. Excess contrasting removed at 2 min. and the grids were air dried for a sufficient time. The observation and recording of the samples was performed using a microscope Jeol model JEM-1010 operated at 80 keV and coupled to a digital camera model MTI CCD-300-RC.

Figure 2:
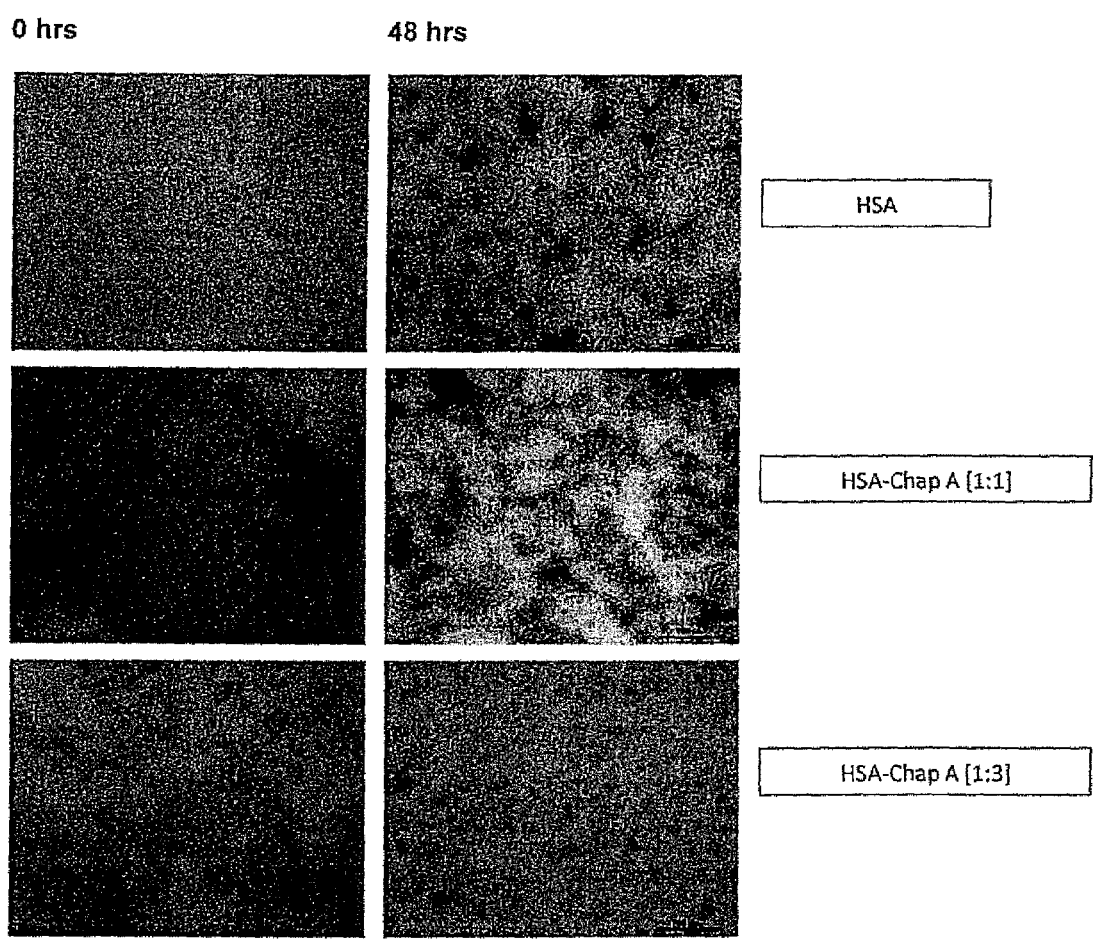
FIG. 2: It shows transmission electron micrographs of the human serum albumin (HSA) fibrillogenesis process, (3.017 μM) in the presence of chaperonin A (3.017 μM and 9.051 μM), incubated at 65° C. for 72 hrs. in Tris (pH 7.4, 20 mM).

FIG. 2 shows that in the absence of chaperonins abundant long fibers are produced and HSA contoured, after 48 hours. In contrast, in the presence of chaperonin A, the fibers are very small and short. It is also observed that at the higher concentration of chaperonin A fibers practically disappear and oligomers are only observed, so that the inhibitory nature of the chaperonin A is inferred.

Example 1—Evaluation of the Modulator Character of Chaperonins in HSA Fiber Formation by Transmission Electron Microscopy (TEM)

The preparation of the samples was performed at a final concentration of 3.017 µM of HSA in Tris buffer (pH=7.4, 20 mM) in the presence or not of the chaperonin A (3.017 µM y 9.051 µM). Incubate at 65° C. for 72 hours. Aliquots were taken every 2 h for TEM study.

HSA solution (5 µl) is placed in 300 mesh copper grids formvar covered for 3 minutes. The excess solution is removed with a micropipette. Subsequently uranyl (5 µL, 2%) is added previously centrifuged at 12,000 rpm for 10 minutes. Excess contrasting removed at 2 min. and the grids were air dried for a sufficient time. The observation and recording of the samples was performed using a microscope Jeol model JEM-1010 operated at 80 keV and coupled to a digital camera model MTI CCD-300-RC.

FIG. 2 shows that in the absence of chaperonins, abundant long and contoured HSA fibers are produced after 48 hours. In contrast, in the presence of chaperonin A, the fibers are very small and short. It is also observed that at the higher concentration of chaperonin A fibers practically disappear and only oligomers are observed, so that the inhibitory nature of the chaperonin A is inferred.

Example 2—Evaluation of Modulating Ability of Chaperonins in Fiber Formation of Human Serum Albumin (HSA)

Preparation of Study Solutions

Thioflavin-T(ThT): Th-T (Sigma, 47 mg) is dissolved in water until 25 mL as final volume.

HSA: HSA (300 µM) is prepared in buffer (glycine, pH=3, 50 mM, NaCl 100 mM) until 10 mL as final volume. The solution is filtered through a syringe filter with acrodisc type 0.20 microns pore (Supelco Analytical).

Chaperonin: chaperonin selected is dissolved in 25 mL of DMSO, as non-limiting example of the Formula I, (75.4 µmol; A, B, C, D,).

Experimental Procedure

250 µL of the HSA solution (300 µM) and the mixture of HSA with chaperonins (300 µM) was taken and placed in the respective wells (polystyrene plates, 96-well Costar 3615, Special Optics Plate) for adding ThT (1 µl) to each well to get a final concentration of 24 µM. Fluorescence signals are measured at $\lambda_{emis.}$=482 nm ($\lambda_{excit.}$=450 nm) in a fluorescence spectrophotometer Infinite M1000, TECAN, Austria. The readings were performed every 20 min at 42° C. All signals are corrected with the background signal, for which a target containing ThT in water is prepared, without the HSA.

Figure 3:
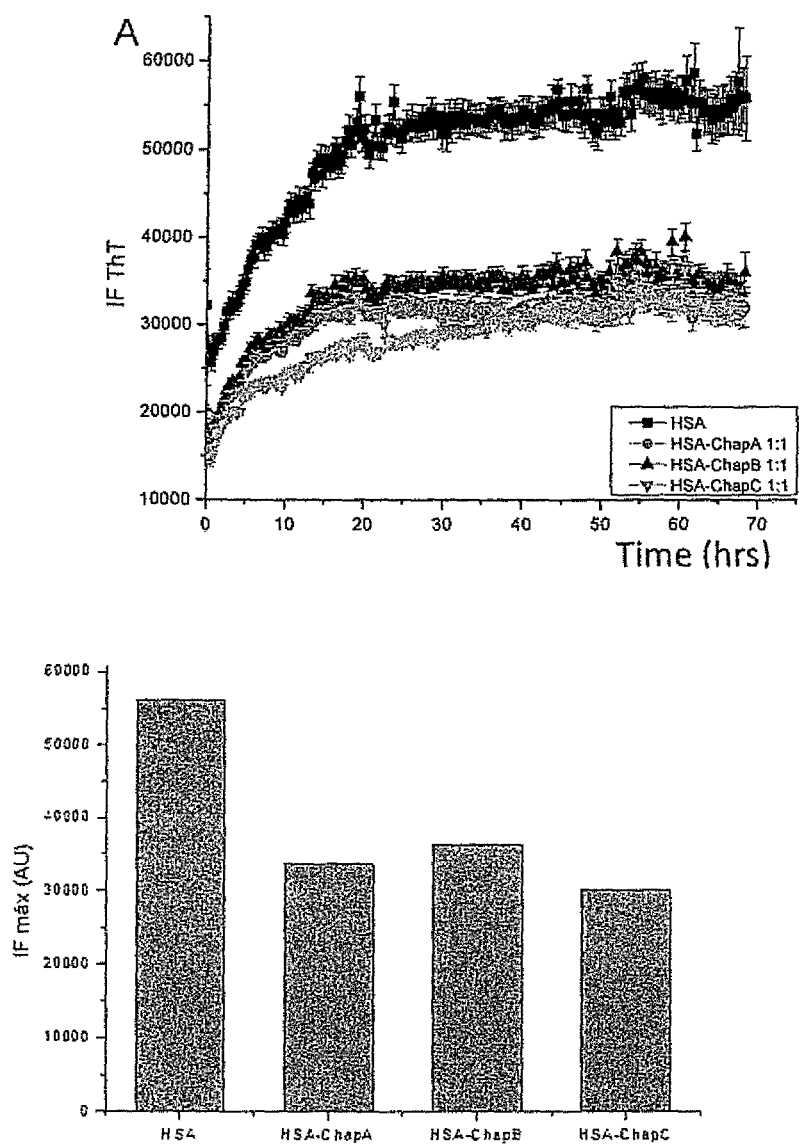
FIG. 3: The kinetics of the HSA fiber formation (300 μM) at 42° C. in glycine buffer (pH=3, 50 mM, NaCl 100 mM) is presented, in the presence or not of tested chaperonins A, B, C, D (300 μM) measured by fluorescence spectroscopy with Thioflavin-T (ThT 24 μM).

FIG. 3 shows the results obtained from the kinetics of the fibers of HSA formation (300 µM) at 42° c. with glycine buffer (50 mM, pH=3; 100 mM NaCl), in presence or not of evaluated chaperonins (300 µM). It is observed that in the process of HAS fibrillogenesis, the lag phase does not show up. When chaperonin was added, a decrease in the fluorescence intensity was observed (FI) of the ThT, which corresponds to a smaller amount of fibrils. This shows the inhibitory capacity of chaperonins in HAS fibrillogenesis process.

Example 3—Evaluation of Modulator Character of Chaperonins in the Kinetics of Fiber Formation of Bovine Serum Albumin (BSA) by Fluorescence Spectroscopy Preparation of Study Solutions Thioflavin-T (ThT): Th-T (Sigma, 10 mg) is dissolved in water and make to a final volume of 5 mL.

BSA: BSA (fraction V, MM: 66 296 Da, 500 mg) was dissolved and make to a final volume of 10 mL with buffer (glycine, pH=3; 50 mM; 100 mM NaCl). The dissolution is filtered through a filter syringe of the acrodisk type with pore 0.45 µm (Sigma-Aldrich). The exact concentration of the BSA, is calculated by considering the reported value of the molar extinction coefficient ($\xi$=43 824 AU·cm$^{+1}$·M$^{-1}$).

Chaperonin: Selected chaperonin, is dissolved as not limited example of Formula I, (75.4 µmol to A, B, C, D, E, F and G, FIG. 1) in 1.2 mL of DMSO and dilute to a final volume of 10 mL with buffer.

Experimental Procedure

250 µL from the BSA solution are taken (100 µM) and BSA with chaperonins mixtures (1 µM) are deposited into the corresponding wells adding ThT (1 µL) to each well to obtain a final concentration of 24 µM. Fluorescence signals are measured at $\lambda_{emis}$=482 nm ($\lambda_{excit}$=450 nm) in a spectrophotometer fluorescence Infinite M1000, TECAN, Austria, (96 wells, cost 3615, Special Optics Plate polystyrene plates). The readings were performed every 10 min after incubation at 65° C. All signals are corrected with the background signal, of which a target containing ThT in water is prepared, without the BSA.

Figure 4:
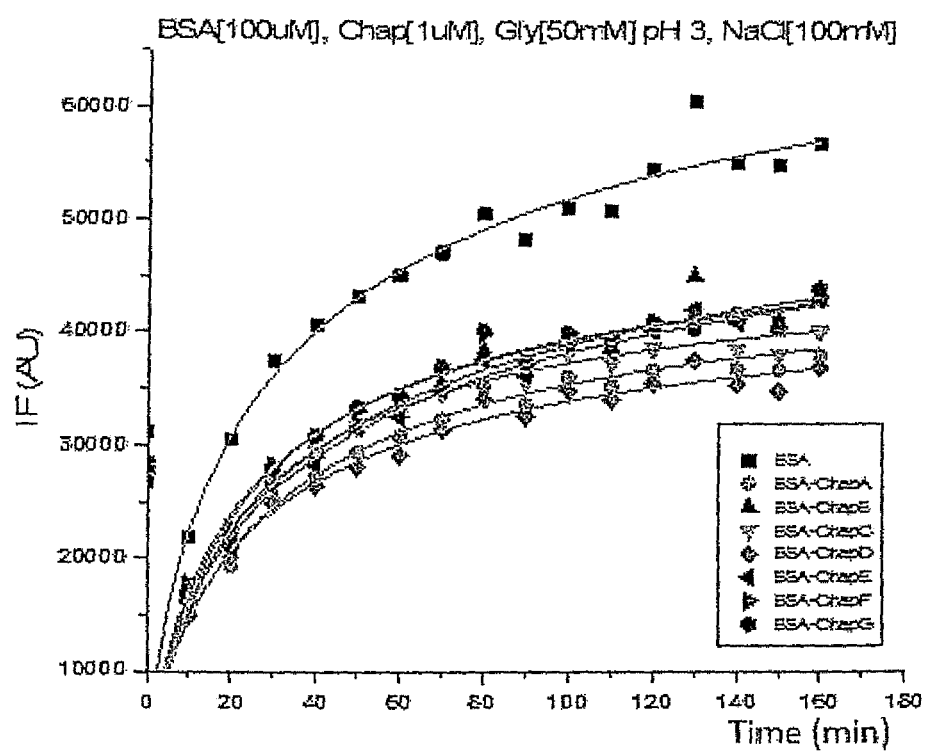
FIG. 4: The kinetics of Bovine Serum Albumin (BSA) fiber formation (100 μM) in the presence or not of chaperonins A, B, C, D, E, F and G (1 μM) is presented at 65° C. in glycine (pH=3, 50 mM; NaCl 100 mM), measured by fluorescence spectroscopy with Thioflavin-T (ThT 24 μM).

FIG. 4 shows the results obtained from the kinetics of the BSA (100 mM) fibers formation at 65° C. with glycine buffer (pH=3; 50 mM; NaCl 100 mM), in presence or not of evaluated chaperonins (1 µM). As noted, the BSA fibrillogenesis process did not show a well-defined lag phase and it stabilized from the 120 min. approximately. When the chaperonin was added, it was appreciated a decrease in the ThT fluorescence intensity (FI), which corresponds to a lower amount of fibrils. This shows that the fibrillogenesis process is inhibited in the presence of the chaperonine.

Example 4—Evaluation of the Modulator Character of Chaperonins in the BSA Fiber Formation by Using Fluorescence Microscopy The sample preparation was carried out similarly to that described in Example 3. The plate is incubated at 65° C. for 3 h. Then, 100 µL of sample is deposited in an Eppendorf tube and ThT is added to achieve a final concentration of 20 µM. The samples were centrifuged at 1300 rpm for 2 minutes. Then 6 µL of sample are deposited on a slide with the cover slip. It is observed through the fluorescence microscope Zeiss Axiostar plus, 50/AC HBO lamp with blue filter. The images are recorded at 10×.

Figure 5:
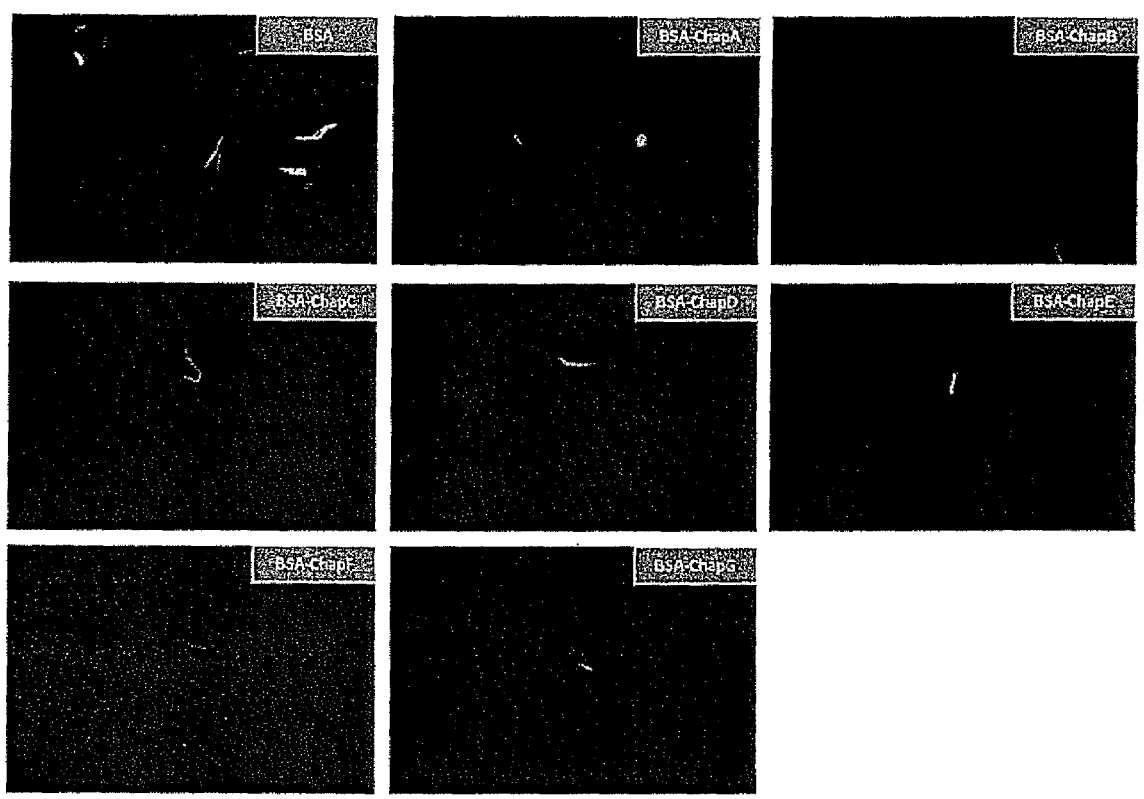
FIG. 5: It shows Fluorescence Electron Microscopy images of BSA fibrillogenesis process (100 μM) in the presence or absence of chaperonins A, B, C, D, E, F and G (1 μM), at 65° C. in Glycine (pH=3, 50 mM; NaCl 100 mM), with Thioflavin-T (ThT, 20 μM).

In FIG. 5, samples of the micrographs obtained at the end of experiment are shown. In the BSA micrograph, without chaperonins, long and abundant fibers were observed. In contrast, when used chaperonins, less abundant short fibers were observed. This result demonstrates the ability of chaperonins to inhibit the protein fibrillogenesis process.

Example 5—Evaluation of the Modulator Character of Chaperonins in the Kinectics of BSA Fiber Formation by Fluorescence Spectroscopy Preparation of Study Solutions Thioflavin T (ThT): 100 mg of ThT (Sigma) were dissolved in water and made up to a final volume of 10 mL.

BSA: BSA (fraction V, MM: 66,296 Da, 500 mg) was dissolved and made up to a final volume of 25 mL in buffer (PBS 0.1 M, pH=8.9, Tris 20 mM, pH=7.4 or Glycine 50 mM, without and with 100 mM NaCl, pH=3). The concentration of BSA is calculated considering the reported value of molar extinction coefficient ($\xi$=43824 AU·cm$^{-1}$·M$^{-1}$).

Chaperonin: the selected chaperonin, as non-limiting example of Formula I, is dissolved (75.4 µmol: A, B, C, D, E, F and G, FIG. 1) in DMSO and made up to a final volume of 10 mL with selected buffer.

Experimental Procedure

BSA solutions (BSA in the absence of chaperonin 50 uM) and mixtures of BSA with chaperonins at the same concentration (molar ratios of BSA:chaperonin: 1:0; 1:0.0025; 1:0.005, 1:0.01, 1 0.02, 1:0.1, 1:1, 1:2) was passed through acrodisc-type syringe filters with 0.2 microns pore (Sigma-Aldrich). These solutions are incubated at 20 and 75° C. temperature, without shaking. Then, a homogeneous aliquot of these mixtures is extracted and ThT (10 mg/mL) is added to obtain a BSA solution with a molar ratio of 50:1 ThT. The fluorescence signals are measured to $\lambda_{emis}$=482 nm ($\lambda_{excit.}$=450 nm) on a Cary Eclipse fluorescence spectrophotometer (cell format) or Infinite M1000, TECAN, Austria, (polystyrene plate format 96 well Costar 3615, Special Optics Plate), both equipped with temperature control. All signals are corrected with the signal line, for which a target containing ThT in water is prepared without BSA.

For the calculation of IC50, the BSA solutions (300 mM) and BSA with chaperonins mixtures at molar ratios of BSA:chaperonin: 1:0, 1:0.01, 1:0.05, 1:0.5, 1:1, 1:2.5; 1:5 were prepared. The samples were treated according to the procedure described above.

In FIG. 6 (Part A), the results of the BSA fibers formation kinetics (50 mM) at 75° C. in PBS (pH=8.9, 100 mM) in the absence and presence of evaluated chaperonins at the same concentration, are shown. As noted, the process of BSA fibrillogenesis does not have a lag phase and the plateau is reached in the first 50 minutes. Generally, there is a decrease in concentration of BSA fibrils in the presence of chaperonins expressed by the decrease of the FIs of the ThT regarding BSA control.

In Part B of FIG. 6, it is observed that in the presence of any of the tested chaperonins, there is a significant decrease of the FIs of the ThT after 150 minutes. This effect is more evident when chaperonins F and G are used, being significantly higher than the effect of the reference compound (chaperonin C or naproxen). This indicates an inhibition in the BSA fibrils formation.

Figure 7:
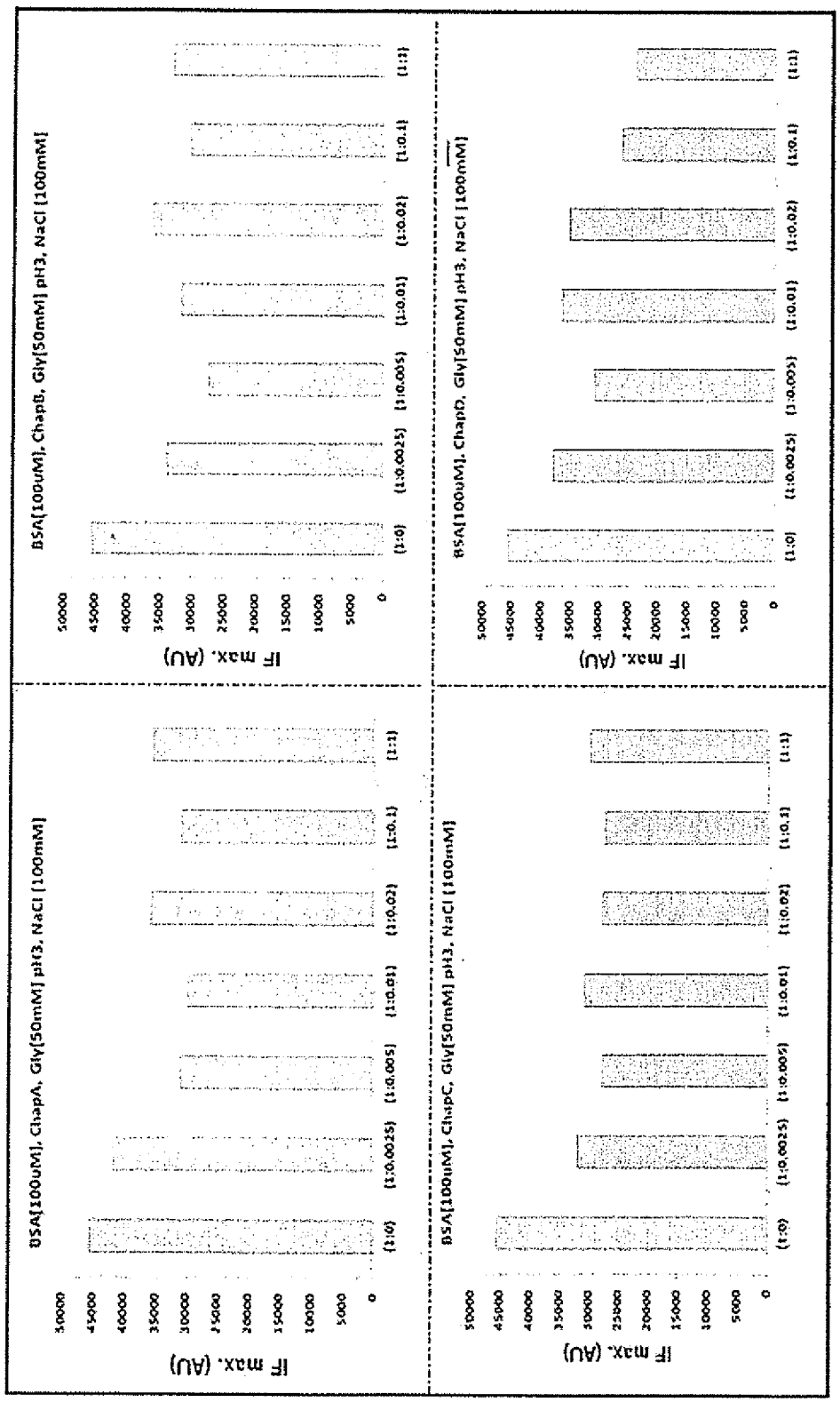
FIG. 7: It shows the chaperonins A, B, C and D concentration effect; as non-limiting examples selected from Formula I; on the kinetics of BSA fibril formation (100 µM; molar ratio BSA:Chap 1:0 1:0.0025; 1:0.005, 1:0.01, 1:0.02, 1:0.1 and 1:1) at 65° C. in glycine (pH=3, 50 mM, NaCl 100 mM) in the presence of ThT (24 µM).

Also in FIG. 7, the results of the process of BSA fibrillogenesis in the presence of chaperonins A, B, C and D in Glycine buffer (pH=3; 50 mM; 100 MM NaCl) was observed. The inhibition of the fibers formation is still effective at BSA molar ratios:chaperonin less than 1:1, to regard to 1:0. In general, it appears that the process of fibrillogenesis is modulated depending on the concentrations used for a same chaperonin, significantly decreasing the concentration of fiber obtained.

In FIG. 8, the table shows the IC50 values, obtained for each evaluated inhibitor, as not limiting example. The calculation is done by interpolating the data by a logarithmic function. It is found that the inhibitory activity of aggregation depends on the chaperonins concentration. The inhibitory activity of chaperonins A and B are similar from each other and twice higher than C. Furthermore, the chaperonin D was 17 times higher than the previous ones. These results agree with those obtained in FIG. 7 and confirm the modulatory activity of chaperonins evaluated in protein aggregation.

Example 6—Evaluation of the Modulator Character of Chaperonins in the BSA Fiber Formation by Transmission Electron Microscopy (TEM)

For the experiment, described in example 5, various aliquots (10 µL) of each sample were taken and there were suitably diluted in the buffer, defined in this example (dilution 1/10 or 1/20). Over copper grids (400 mesh), covered by collodion and carbon, are deposited 6 µL of each sample. After 5 min, the sample excess is removed, using filter paper, and the preparations were stained with $UO_2$ $(AcO)_2$ (1%). TEM images were recorded at 80 kV with an electron microscope JEM-1010, JEOL (Japan).

Figure 9:
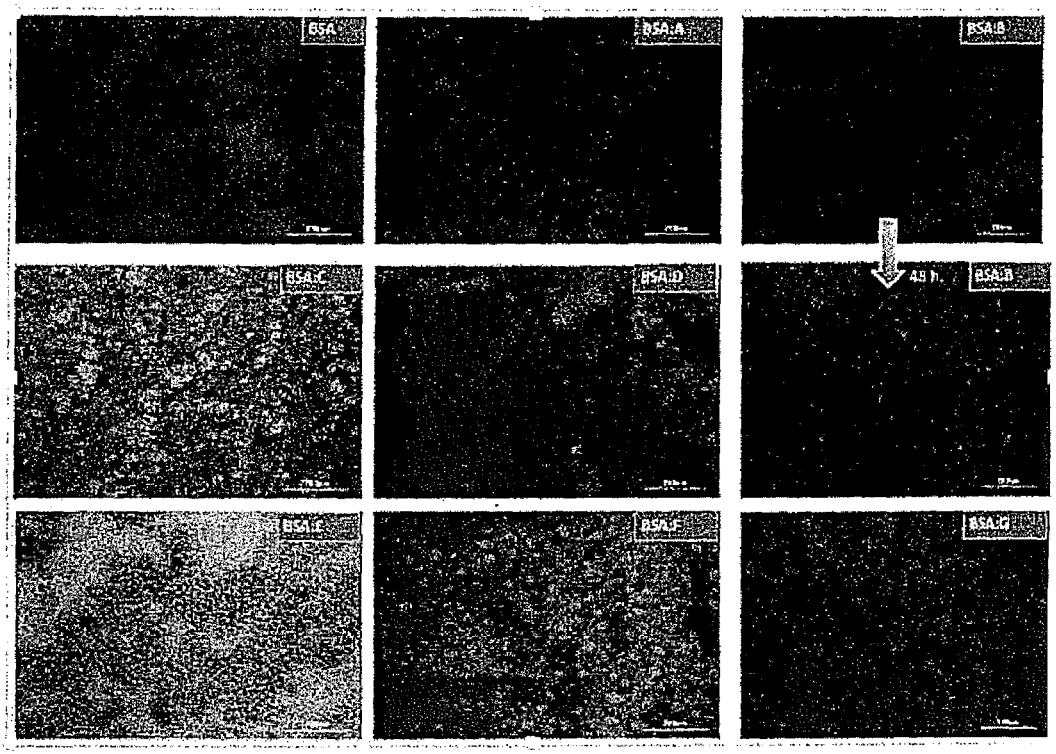
FIG. 9: It shows transmission electron micrographs of the BSA fibrillogenesis process (75 µM) in the presence or not of chaperonins A, B, C, D, E, F and G (50 µM) selected as Formula I non-limiting examples, in Tris (pH=7.4, 20 mM), at 75° C., 3 h, without stirring.

The modulatory action in the BSA fibrillogenesis of the selected chaperonins was evaluated by TEM technique, which allows observing the amyloid fibers whose diameter is approximately 8 nm. Examples of micrographs obtained for experiments with BSA (50 mM) and BSA Chaperonins A, B, C, D, E, F and G (molar ratio 1:1) are shown in FIG. 9.

In the first micrograph, it showed the presence of long and contoured fibers of BSA. In all other micrographs, which represent the experiments in the presence of different chaperonins, it can be seen amorphous and circular structures defined as oligomers. These results demonstrate the inhibitory or disaggregating effect of the selected chaperonins over the fibers, as non-limiting examples of Formula I.

Example 7—Evaluation of the Modulator Character of Chaperonins in the Kinetics of IAPP Fibril Formation (20 TO 29 AA) by Fluorescence Spectroscopy Preparation of Study Solutions Thioflavin T (ThT): 100 mg of ThT (Sigma) were dissolved in water and made up to a final volume of 10 mL.

IAPP fragment 20-29 was synthesized according to the procedure described (Kates, E, and Albericio F. in Solid-Phase Synthesis, Marcel Dekker Inc. New York, 2000; Hood, C A, et al in Pept. Sci 2008, 14, 97-101). The peptide was purified by semipreparative reverse high performance liquid chromatography (SP-HPLC for its acronym in English Semipreparative Reversed Phase High Performance Liquid Chromatography) and its purity was greater than 95%. The expected molecular mass (MM: 1029 Da) was confirmed by mass spectrometry (ESI-MS, its acronym in English Electrospray Ionization Mass Spectrometry).

Chaperonin: the selected chaperonin, as non-limiting example of Formula I, was dissolved in 1.2 mL of DMSO and made up to a final volume of 10 mL with buffer (PBS 100 mM, pH 7.4; NaCl 100 mM).

Experimental Procedure

The solution of IAPP (20-29, 100 µM) with and without chaperonins (100 µM) was incubated at 25° C. in methacrylate cells (Sigma-Aldrich) volume 4.5 mL, 10 mm path length, in the presence of ThT (20 µM) at 50:1 molar ratio of IAPP:ThT, and the cells were stirred during the kinetic. The IF (Cary Eclipse spectrofluorometer) were continuously recorded at $\lambda_{emis}$=482 nm ($\lambda_{excit.}$=450 nm) with a bandwidth of 5 nm. All signals are corrected with the background signal with ThT in water, used as blank, in the absence of protein.

Figure 11:
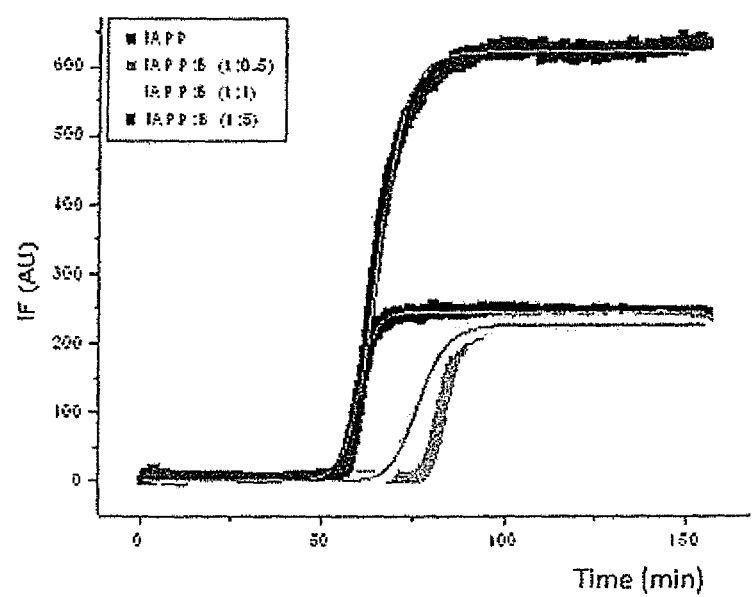
FIG. 11: The effect of the concentration of the chaperonin B (molar ratio IAPP:Chap B 1:0.5; 1:1; 1:5) is presented as a Formula I non-limiting example, on the kinetics of fibril formation of (APP fragment 20-29 (100 µM) at 25° C. in PBS (pH 7.4, 100 mM, NaCl 100 mM). Molar ratio IAPP:ThT, 50:1.

In FIG. 10 (part A), the modulating effect of chaperonins A, B, C, D, E and F are presented in fibril formation of IAPP fragment 20-29 at 25° C. All chaperonins, in the concentration tested (molar ratio peptide:chap 1:1), modulated this process. E and F chaperonins accelerated the IAPP fiber formation. Instead, the chaperonins A, B, C and D increased the average time of the fibers formation, therefore, delayed the fibrillogenesis process (FIG. 10, Part B). In the case of chaperonin B, this inhibitory behavior was kept for protein:chaperonin at molar ratios less than or equal to 1:1 (FIG. 11). However, when the molar ratio is higher, the process was accelerated and the concentration of formed fibers increased.

Example 8—Evaluation of Cell Viability of Cerebellar Granule Cells (CGC) in the Presence of IAPP 20-29 (Monomer and Aggregated). Cytoprotective Effect of Chaperonins Sample Preparation.

The solutions fragment of IAPP 20-29 (MM 1029 Da) are prepared in PBS buffer (100 mM, pH 7.4; NaCl 100 mM). Monomeric peptide concentration was 5.8 mM and the aggregation peptide was 32.6 µM in DMSO. Protein concentration is calculated using the calibration curve.

Chaperonin: solutions of chaperonin B and D (25 µM), selected as non-limiting examples of Formula I, are prepared in 1.2 mL of DMSO and dilute with the buffer to obtain a final volume of 10 m. Curcumin (5.5 mM) used as reference compound was prepared in ethanol. (Yang, F. et al. in J. Biol Chem 2005, 280, 5892-5901).

Experimental Procedure

Viability tests were performed according to the procedures reported by Moran et al. (White, S. and Moran, J. in J. Neurochemistry International, 2011, 58, 934-42). Cell cultures of cerebellar granule cells are used (CGC 8 DIV).

In particular, in this invention, the viability of CGC cell cultures was assessed with the 20-29 fragment of IAPP, in its monomeric and aggregated form or with the mixtures of protein:chaperonin at different molar ratios. Briefly, in all samples of CGC, half of the volume of medium is removed to add, independently, the quantities of tested protein or mixtures of peptide:chaperonin with different molar ratios (1:0.3 or 1:1). Then, the cell culture medium enriched rejoins and again incubated for 20 hours. Viability levels are estimated using the MTT assay. (Benitez, A. and J. Morán in J. Neurosci Res 2003, 71, 383-96).

Cell viability of the CGC cell culture exposed to the IAPP fragment 20-29, in its monomeric or aggregated form, and in the presence or absence of selected chaperonins was performed using curcumin, as a reference compound, by their reported disintegrating activity. (Yang, F. et al. in J. Biol Chem 2005, 280, 5892-5901).

Figure 12:
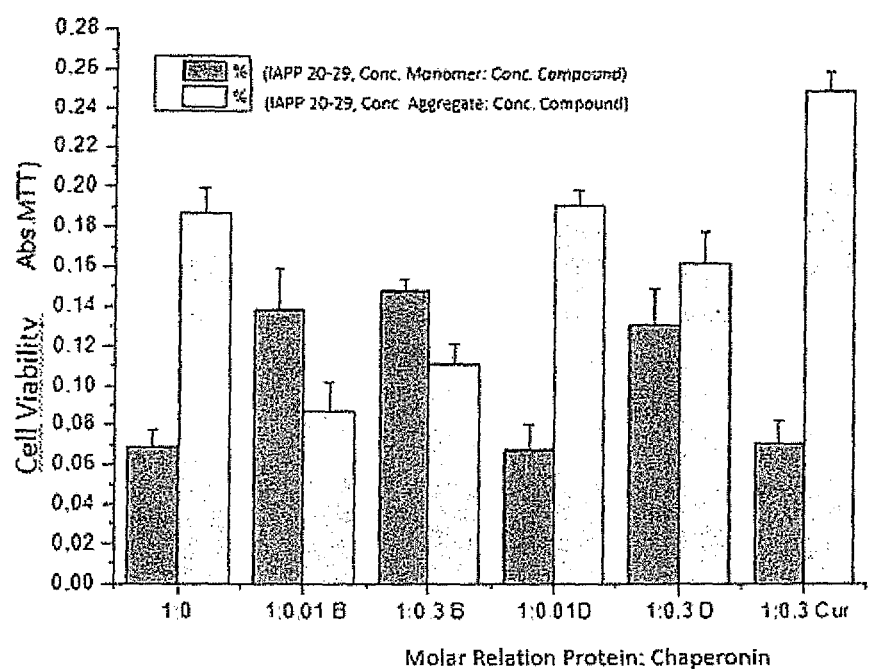
FIG. 12: It shows the evaluation of cell viability in cell cultures of rat Cerebellar Granular Cells (CGC) exposed to IAPP fragments (fragment 20-29 of (APP: non aggregated and aggregated monomer) in the presence or absence of chaperonins B and D, selected as Formula I non-limiting examples. Reference compound: Curcumin.

In FIG. 12, the results of the assessment of cell viability was observed by MTT assay, which were analyzed by the one-way ANOVA statistical test, followed by a posteriori LSD test (LSD for its acronym in English Least Significant Difference).

The results indicated that the cytotoxic effect of the protein in its monomeric form is nearly three times more cytotoxic in the GCC that its aggregated form ($p<0.05$). Moreover, when cells are exposed to the monomer in the presence of chaperonins was found that viability is twice higher for the chaperonin B at the two molar ratios tested, being significantly different from the rest of the other compounds tested ($p<0.05$). In the case of chaperonin D, the viability is almost twice as high for a molar ratio of 1:0.3 and were significantly different ($p<0.05$) when cells are exposed to the monomer alone. In contrast, in the presence of curcumin, no significant differences ($p>0.05$) were observed. This is consistent with some reports indicating that curcumin acts as a potent cytoprotective when cells are exposed to proteins in an aggregated form and do not make this function against the monomer. (Yang F. et al. in J. Biol Chem 2005, 280, 5892-5901).

The cytoprotective effects of novel Chaperonins evaluated on CGC in the presence of cytotoxic monomer 1APP, could be explained by the type mechanism of action: inhibition of aggregation, the aggregation reduction or monomer removal, among others.

In the case of the aggregated form of the fragment 20-29 of IAPP in the presence of the chaperonin D, the viability of CGC does not differ significantly from cells exposed to the aggregated fragment of IAPP 20-29 ($p>0.05$). As expected, curcumin showed a marked cytoprotective effect that is statistically different ($p<0.05$) from the rest of the study groups.

Example 9—Evaluation of the Apoptotic Effect of the IAPP Fragment 20-29 (Monomer and Aggregated) and Chaperonins on Cerebellar Granule Cells (CGC)

Sample Preparation.

Solutions of IAPP fragment 20-29 (1029 Da MM) are prepared in PBS buffer (pH=7.4, 100 mM; NaCl 100 mM). Monomeric peptide concentration was 5.8 mM and the aggregated peptide was 32.6 µM in DMSO. Protein concentration is calculated using the calibration curve.

The Chaperonins solutions B and D at 25 µM in DMSO, each one, and curcumin (5.5 µM) in ethanol, was prepared.

Experimental Procedure

Apoptosis trials are performed according to the procedures reported by J. Moran et al. (in J. Neurochem. 1999, 73, 568-77), using CGC cultures of 8 DIV.

The apoptotic effect of proteins and the cytoprotective effects of Chaperonins B and D, as non-limiting examples selected from Formula I, are evaluated in cell cultures of CGC and used curcumin as reference compound. Briefly, in all samples were removed from the culture medium, the half volume to be added, independently, the quantities of tested protein (IAPP, in its monomeric form and aggregated), mixtures of protein:chaperonins at different molar ratios (1:0.3 or 1:1), or chaperonins. Then, the cell culture medium enriched rejoins and again incubated for 4 hours additional. Cellular apoptosis is estimated by determining of levels caspase-3 immunofluorescent (J. Moran et al. in J. Neurochem. 1999, 73, 2, 568-77), with the use of a spectrofluorometer Bioteck-Synergy.

Figure 13:
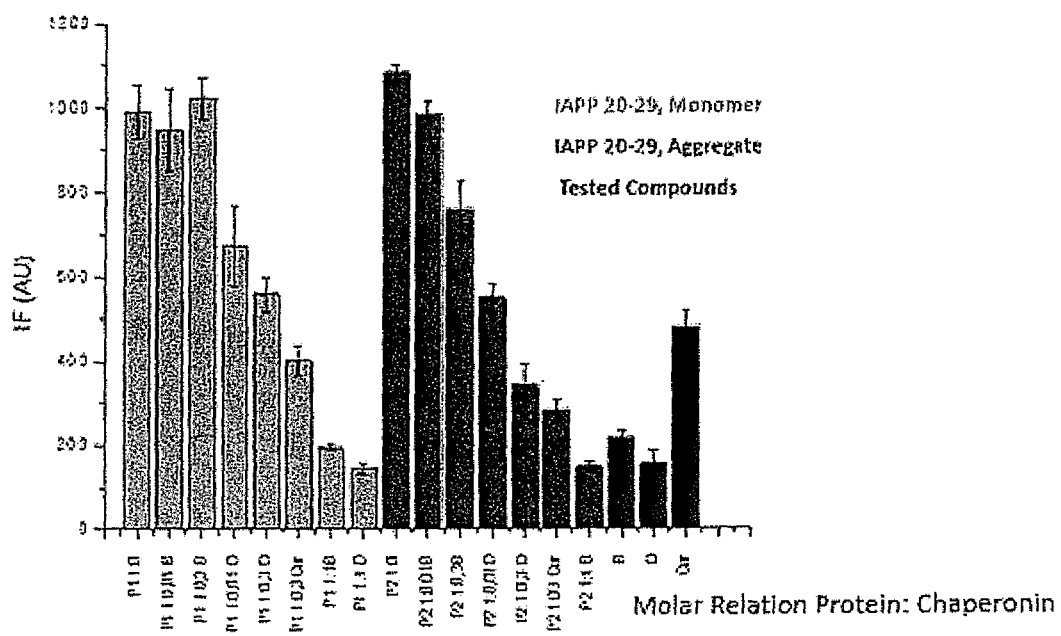
FIG. 13: Evaluation of cell apoptosis in cell cultures of rat Cerebellum Granular Cell (CGC) exposed to (APP fragments (fragment 20-29 of IAPP: non aggregated and aggregated monomer) in the presence or absence of chaperonins B and D were selected as Formula I non-limiting examples. Reference compound: Curcumin.

The levels of caspase-3 of GCC exposed to different forms of fragment 20-29 of monomeric or aggregated IAPP were not significantly different ($p>0.05$), and were obtained the higher apoptotic levels observed (FIG. 13).

It was found that the addition of mixtures of IAPP (fragment 20-29 of monomeric IAPP or aggregated to it) with chaperonins in the CGC, reduced the levels of caspase-3 significantly. So, six times more inhibition is obtained when the maximum concentration of chaperonins B is used and D with regard to the controls without chaperonins. These results demonstrate that novel tested chaperonins inhibit and/or reduce the cytotoxic effect caused by the IAPP on CGC cells that cause programmed cell death.

Example 10—Evaluation of the Protective Effects of Chaperonins B, C and D on Cerebellar Granule Cells (CGC)

Sample Preparation.

Chaperonins solutions B, C and D are prepared (20 µM) in DMSO.

Experimental Procedure. Apoptosis assays are performed according to the procedures reported by J. Moran et al. (J. Neurochem. 1999, 73, 568-77). The CGC cultures with 8 DIV were used. The experiments were performed in triplicate.

The effect regenerator and/or protector chaperonins B, C and D, as non-limiting examples selected from Formula I, are assessed in CGC cultures at low potassium (−KCl). The culture medium of the wells with 25 mM KCl (+KCl) is removed by aspiration and replaced with a medium −KCl (5 mM).

Chaperonins B, C and D (25 µM) were added separately, at the initial time (Group I) or after 4 h. (Group II) of the induction of pro-apoptotic stimulus (−KCl) and incubated 4 h additional, including the two control groups: —KCl and +KCl. Apoptosis was estimated by determining levels immune fluorescent caspase-3 (J. Moran et al. in J. Neurochem. 1999, 73, 2, 568-77), with the use of a spectrofluorometer Synergy-Bioteck.

Figure 15:
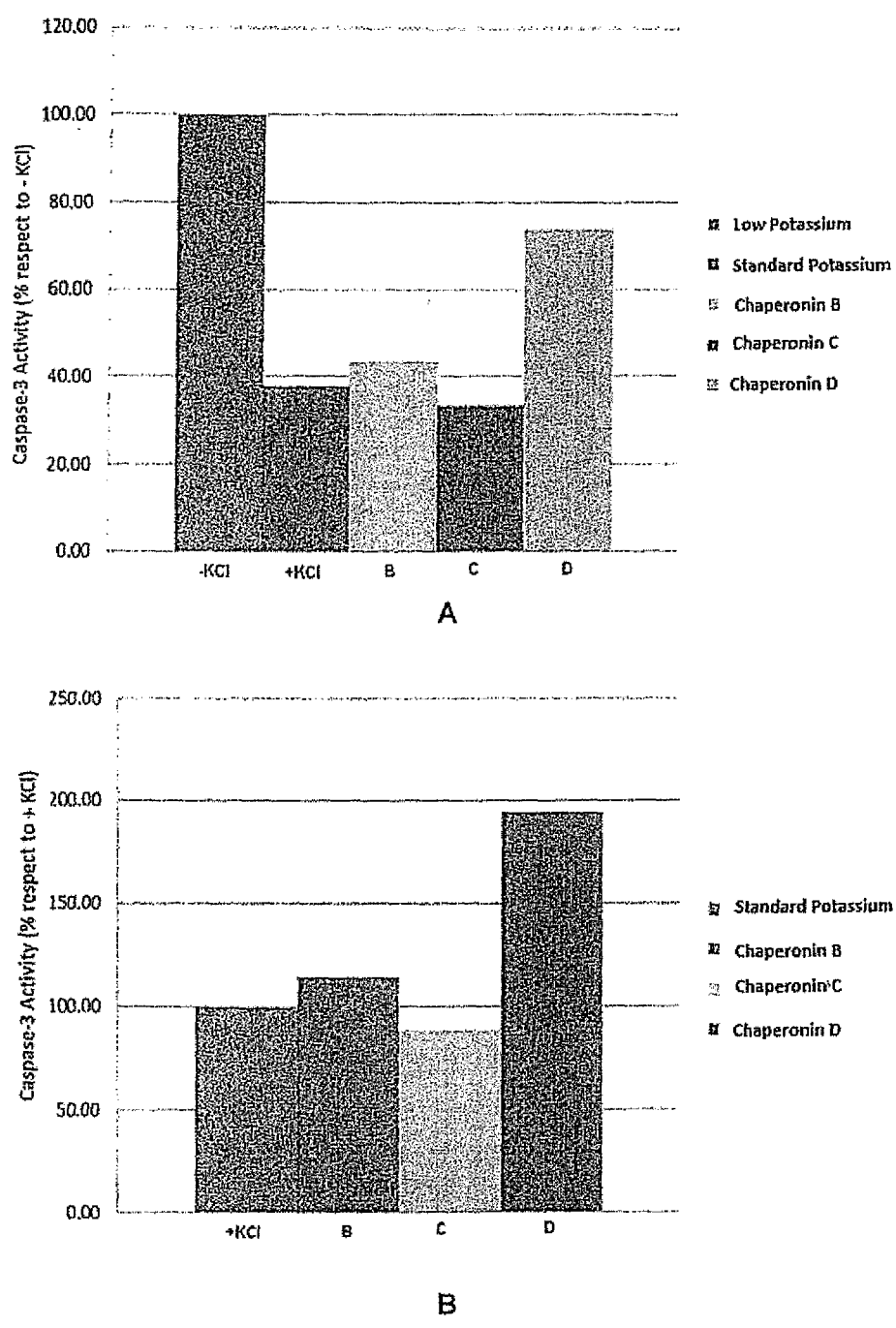
FIG. 15: It shows the evaluation of the protective activity and/or reconditioned of chaperonins B, C and D, when administered to rat Granular Cerebellum (CGC) cell cultures 4 h. after that they were exposed to a low potassium culture medium (−KCl). Part A of the figure presents the results regarding −KCl (protective effect) and Part B of the figure presents the results regarding the control of standard potassium (+KCl) (reconditioned effect).

FIGS. 14 and 15 show the results obtained.

In FIG. 14, a reduction of the levels of caspase-3 in Group I of GCC with respect to the −KCl control group was observed. This reduction was 92, 80 and 78% for the samples treated with B, C and D, respectively (Part A, FIG. 14). On the other hand, the levels of caspase-3 (Part B, FIG. 14) for samples with chaperonins B, C and D of Group I were lower in a 84, 54 and 52%, respectively, relative to +KCl control group. These results demonstrate the protective effect of evaluated chaperonins with respect to both controls.

In FIG. 15 (part A) shows that in Group II, the level of caspase-3 was lower for samples treated with chaperonins B, C and D, (56%, 66% and 26%, respectively) with regard to −KCl control group, so that a protective effect is evident. However, if we compare the level of caspase-3 with the +KCl control (FIG. 15, Part B), we show, in the case of chaperonin B and C, that there are no appreciable differences. In the case of the chaperonin 0 level of caspase-3 is a 94% higher relative to +KCl control. In general, it can be concluded that the presence of chaperonins B and C have a regenerating effect similar to the induced by +KCl medium.

Finally, these results demonstrate the protective effects of Chaperonins B, C and D, on the apoptosis induced since they positively compensated the stressful stimulus.

What is claimed is:

1. A method for reducing the cytotoxic effect of a β-folded amyloidegenic protein comprising:
    adding a chaperonin with respect to a β-folded amyloidegenic protein, said chaperonin comprises a compound of Formula I;

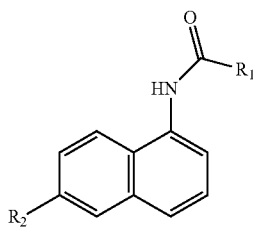

I wherein; $R_1$: -alkylenyl-C(O)NH-alkylenyl-$R_3$, -alkylenyl-C(O)O—$R_4$;
$R_3$: —COOH, —OH, —SH, —$NH_2$, —NH-alkyl-, —NH-dithiocarbamate-alkyl, —N-alkyl-dithiocarbamate alkaline earth metal salts; or salts of the above listed groups, pharmaceutically acceptable, for the treatment of an amyloidegenic disease;
$R_4$: succinimidyl group; and
$R_2$: —H, -alkyl.

2. The method of claim 1, wherein (a) further comprising inhibiting, reducing and refolding under controlled acceleration and/or disaggregation of soluble oligomers, prefibrilar, protofibril and fiber structures and amyloid plaques.

3. The method of claim 1, wherein Formula I further comprises: $N^1$-(2-aminoethyl)-$N^4$-(1-naphthyl) succinimide, methyl(2-{[4-(1-naphthylamino)-4-xobutanoyl] amino}ethyl)dithiocarbamate, N-[4-(1-naphthylamino)-4-oxobutanoyl]-β-alanine, 6-{[4-(1-naphthylamino)-4-oxobutanoyl]amino}hexanoic acid, $N^3,N^{3'}$-butane-1,4-bis ($N^1$-1-naftilsuccinamida)$N^1$-(2-aminobutyl)-$N^4$-(1-naphthyl) succinimide or salts, prodrugs or pharmaceutically acceptable solvates thereof.

4. The method of claim 1, wherein the disease is one selected from Diabetes mellitus (type II), Alzheimer's disease, Parkinson's Disease, Huntington's Disease, and Transmissible Spongiform Encephalopathies.

5. The method of claim 1, wherein (a) further comprises preventing the formation of soluble oligomers, prefibril, protofibril and fiber structures and amyloid plaques.

6. The method of claim 1, further comprising reducing the cytotoxic effect of a β-folded structure present in the disease.

7. A method for cytotoxic protection of cerebellar granule cells (CGC) comprising:
    (a) providing a chaperonin with respect to a protein, said chaperonin comprises a compound of Formula I;

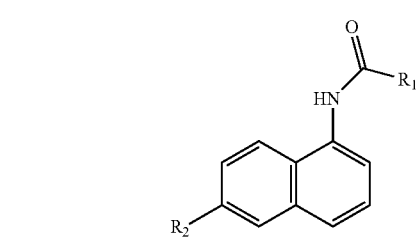

I wherein; $R_1$: -alkylenyl-C(O)NH-alkylenyl-$R_3$, -alkylenyl-C(O)O—$R_4$;
$R_3$: —COOH, —OH, —SH, —$NH_2$, —NH-alkyl-, —NH-dithiocarbamate-alkyl, —N-alkyl-dithiocarbamate alkaline earth metal salts; or salts of the above listed groups, pharmaceutically acceptable, for the treatment of an amyloidegenic disease;
$R_4$: succinimidyl group; and
$R_2$: —H, -alkyl.

* * * * *